(12) United States Patent
Kim et al.

(10) Patent No.: US 8,642,793 B1
(45) Date of Patent: Feb. 4, 2014

(54) BIOSURFACTANT PRODUCED BY AUREOBASIDIUM PULLULANS

(71) Applicant: Gyeongbuk Institute for Marine Bio-industry, Gyeongsangbuk-do (KR)

(72) Inventors: Jong Shik Kim, Gyeongsangbuk-do (KR); Nyun Ho Park, Gyeongsangbuk-do (KR); Choong Gon Kim, Gyeongsangbuk-do (KR)

(73) Assignee: Gyeongbuk Institute for Marine Bio-Industry, Gyeongsangbuk-do (KR)

( * ) Notice: Subject to any disclaimer, the term of this patent is extended or adjusted under 35 U.S.C. 154(b) by 0 days.

(21) Appl. No.: 13/692,681

(22) Filed: Dec. 3, 2012

(30) Foreign Application Priority Data

Aug. 24, 2012 (KR) .................... 10-2012-0093185

(51) Int. Cl.
*C07C 59/147* (2006.01)
(52) U.S. Cl.
USPC .............. 554/121; 554/213; 554/23; 554/8; 554/1
(58) Field of Classification Search
None
See application file for complete search history.

(56) References Cited

FOREIGN PATENT DOCUMENTS

| JP | 2839307 B | 10/1998 |
|---|---|---|
| KR | 10-2009-0080536 A | 7/2009 |
| KR | 10-0961055 B | 5/2010 |
| KR | 10-1019012 B | 3/2011 |

*Primary Examiner* — Yate K Cutliff
(74) *Attorney, Agent, or Firm* — Frommer Lawrence & Haug LLP; Ronald R. Santucci

(57) ABSTRACT

Disclosed is a novel compound having biosurfactant activity that is produced by *Aureobasidium pullulans* L-3-GPY strains (KCCM11200P).

The novelty of the structure of the compound having biosurfactant activity was evaluated using spectroscopy, and it was determined that the biosurfactant produced by the strains has excellent surfactant activity.

Active ingredients of the biosurfactant may be used for various purposes, for example, for producing a composition for washing and cleaning agents. Furthermore, they can be used in a variety of industrial fields where chemically synthesized surfactants are used such as medicines, foods, cosmetics, onshore and offshore oil decontamination, degradation of oil and fat in treatment tanks, and the like where chemically synthesized surfactants are used.

4 Claims, 14 Drawing Sheets

WATER  CULTURE MEDIUM  L9

BIOSURFACTANT PRODUCED BY *AUREOBASIDIUM PULLULANS*

CROSS-REFERENCE TO RELATED APPLICATION

This application claims under 35 U.S.C. §119(a) the benefit of Korean Patent Application No. 10-2012-0093185 filed Aug. 24, 2012, the entire contents of which are incorporated herein by reference.

BACKGROUND (a) Technical Field

The present invention relates to a novel biosurfactant produced by *Aureobasidium pullulans*.

(b) Background Art

The present invention relates to a biosurfactant produced by *Aureobasidium pullulans*) sp. L-3-GPY that is a biosurfactant-producing strain.

A surfactant is a substance having both a hydrophilic moiety and a hydrophobic moiety in a single molecule. This characteristic can change the nature of the surface of a material and/or the interface between materials, thereby reducing a material's surface tension. In an aqueous phase, a surfactant reduces the attractive forces between water molecules. As the concentration of the surfactant increases, a micelle structure can form. A micelle structure is an aggregate of surfactant molecules consisting of external hydrophilic moieties and internal hydrophobic moieties. When a surfactant is placed in a hydrophobic solution, such as a hydrocarbon solution, the surfactant can form an emulsion. Surfactants have dispersibilty, permeability, wettability, emulsifying properties, bubble-forming properties, and the like. Surfactants allow for biodegradation of microorganisms by increasing detachment and solubility of petroleum hydrocarbons (Deshpande et al, 1999. Water Res., 33, 351-360; Doong and Lei, 2003. J. Hazard Mater., 96, 15-27).

While surfactants have been synthesized in small quantities from oil and fat in the past, surfactants are currently chemically synthesized on an industrial mass production scale from coal, oil, and the like. Surfactants are widely used in various industries such as electrical, electronics, construction, machinery, printing, paper manufacturing, and textile industries. However, chemically synthesized surfactants are manufactured via a complicated process, are threatening to aquatic ecosystems due to their formation of bubbles on water surfaces thereby blocking the penetration of sunlight and oxygen, and become a cause of water pollution due to eutrophication induced from phosphates that are formed from phosphorus added to the surfactants to improve detergency. In addition, chemically synthesized surfactants are not easily degradable, due to very low biodegradability, and they readily accumulate in the ecosystem, thereby causing serious environmental problems. In contrast, biosurfactants, surfactants that are intracellularly or extracellularly produced by microorganism strains such as yeast, fungi, and bacteria (Lee et al, 2002. Kor. J. life science, 12, 745-751) are biodegradable and are eco-friendly materials with lower toxicity than synthetic surfactants. Furthermore, biosurfactants can be used for highly specific purposes due to their complex chemical structures and they are not easily synthesized by conventional methods. Additionally, biosurfactants are very useful since they have similar physical and chemical effects to chemically synthesized surfactants, such as surface tension reduction and temperature and pH stability enhancement (Ishigami et al., 1987. Chem. Lett., 763).

Biosurfactants have been widely used in various industrial fields where chemically synthesized surfactants are used such as medicines, foods, cosmetics, detergents, secondary recovery of crude oil, pulp and paper industry, onshore and offshore oil decontamination, degradation of oil and fat in treatment tanks, and the like.

In general, *Aureobasidium pullulans* strains are known to produce a polysaccharide called beta-glucan. Beta-glucan has an immune stimulant effect and is found in the cell walls of yeast, mushrooms, grains, and the like. Beta-glucan activates the immunity of normal human cells. This suppresses the proliferation of cancer cells and the recurrence of cancer, reduces blood sugar level and blood cholesterol level, and improves lipid metabolism thereby suppressing the formation and accumulation of body fat.

However, it has not yet been reported that *Aureobasidium pullulans* strains produce biosurfactants.

The above information disclosed in this Background section is provided solely for enhancing the understanding of the background of the invention and, therefore, it may contain information that is not prior art already known in this country to a person of ordinary skill in the art.

SUMMARY OF THE DISCLOSURE

The present invention has been made in an effort to solve the above-described problems associated with the prior art.

Accordingly, the present inventors have extracted a compound produced by *Aureobasidium pullulans* strains having a biosurfactant component, confirmed the activity thereof, and verified the novelty of the compound.

In one aspect, the present invention provides a compound produced by *Aureobasidium pullulans* strains.

In another aspect, the present invention provides use of a compound produced by *Aureobasidium pullulans* strains as a biosurfactant.

Other aspects and exemplary embodiments of the invention are discussed infra.

In an exemplary embodiment, the present invention provides a compound represented by Formula 1 below and produced by *Aureobasidium pullulans* L-3-GPY strains.

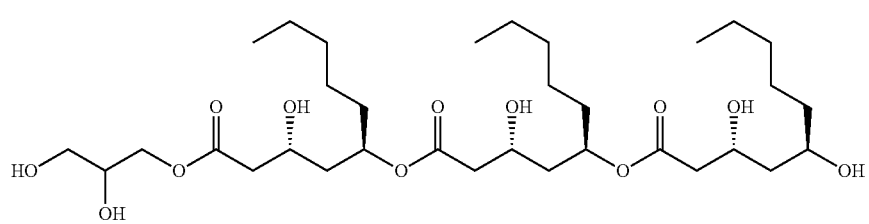

Formula 1

In another exemplary embodiment, the present invention provides a composition for washing and cleaning agents including the biosurfactant of Formula 1.

The above and other features of the invention are discussed infra.

BRIEF DESCRIPTION OF THE DRAWINGS

The above and other features of the present invention will now be described in detail with reference to certain exemplary embodiments thereof illustrated by the accompanying drawings which are given hereinbelow by way of illustration only, and thus are not limitative of the present invention, and wherein.

Figure 1:
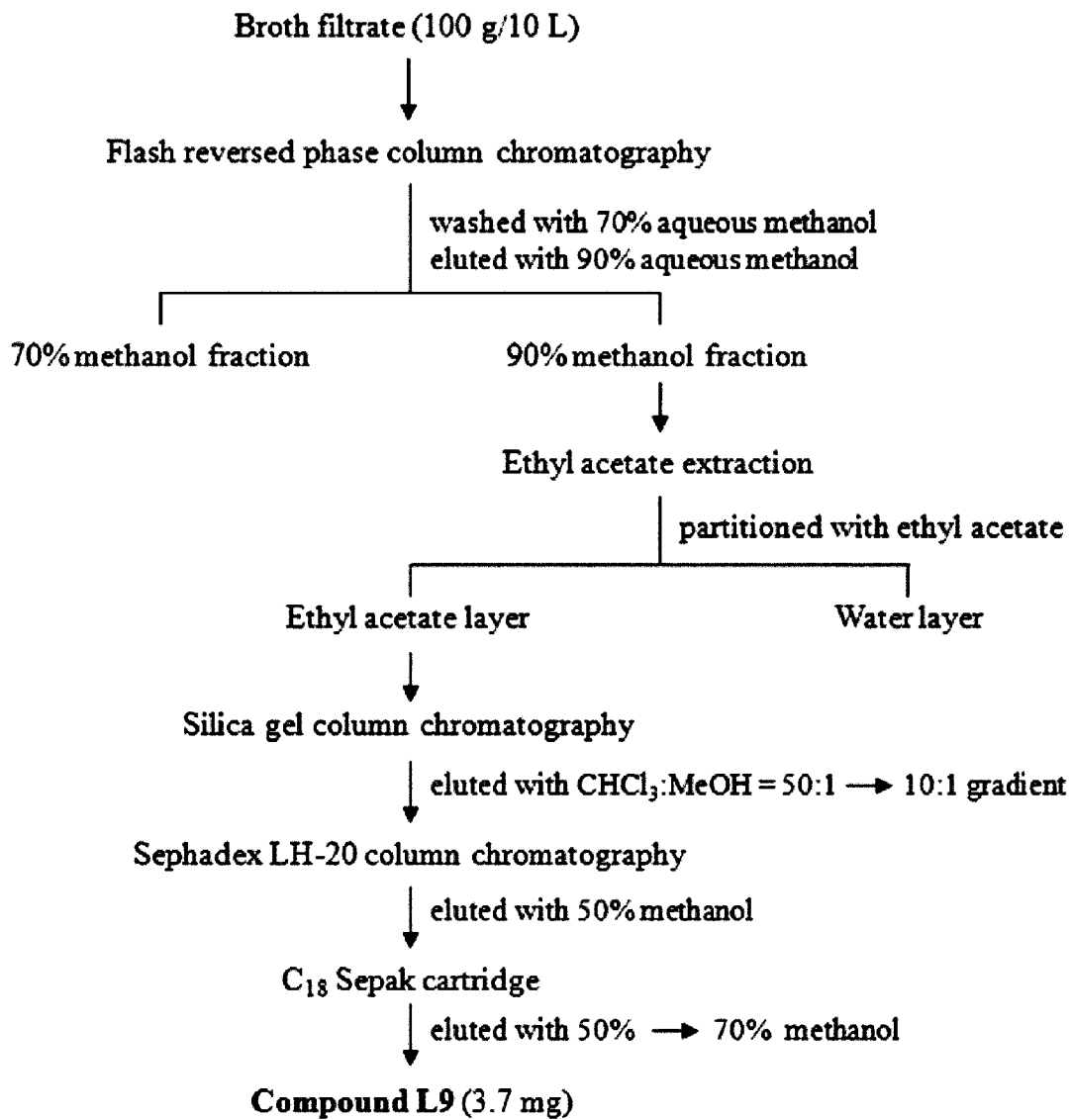
FIG. 1 shows an isolation and purification process of active ingredient L9 according to an embodiment of the present invention.

It should be understood that the appended drawings are not necessarily to scale, presenting a somewhat simplified representation of various preferred features illustrative of the basic principles of the invention. The specific design features of the present invention as disclosed herein, including, for example, specific dimensions, orientations, locations, and shapes will be determined in part by the particular intended application and use environment.

In the figures, reference numbers refer to the same or equivalent parts of the present invention throughout the several figures of the drawing.

DETAILED DESCRIPTION

Hereinafter reference will now be made in detail to various embodiments of the present invention, examples of which are illustrated in the accompanying drawings and described below. While the invention will be described in conjunction with exemplary embodiments, it will be understood that present description is not intended to limit the invention to those exemplary embodiments. On the contrary, the invention is intended to cover not only the exemplary embodiments, but also various alternatives, modifications, equivalents and other embodiments, which may be included within the spirit and scope of the invention as defined by the appended claims.

According to an embodiment of the present invention, a compound represented by Formula 1 below is produced by *Aureobasidium pullulans* L-3-GPY strains (KCCM11200P).

Formula 1

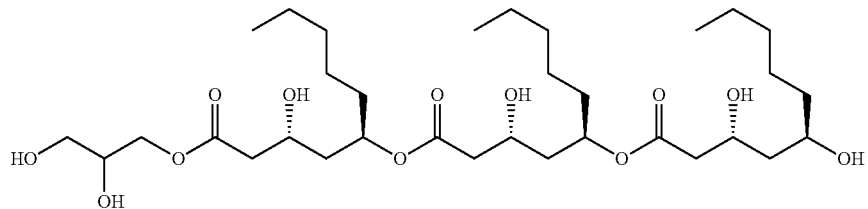 [SMILES: CCCCC[C@@H](O)C[C@@H](O)CC(=O)O[C@H](CCCCC)C[C@@H](O)CC(=O)O[C@H](CCCCC)C[C@@H](O)CC(=O)OCC(O)CO]

In an exemplary embodiment, a material having the structure of Formula 1 is a biosurfactant. A biosurfactant is an amphiphilic material, i.e., lipid or a derivative thereof, present in a living body which includes a hydrophilic moiety and a hydrophobic moiety in a single molecule. A biosurfactant is a comprehensive term including all surfactants derived from living organisms, but refers to a surfactant produced by microorganisms herein. The biosurfactant has lower toxicity and higher biodegradability than conventional synthetic surfactants, thereby solving problems of environmental pollution. Biosurfactants can be used for highly specific purposes due to their complex chemical structures and they are not easily synthesized by conventional methods. Additionally, biosurfactants are very useful since they have similar physical and chemical effects to chemically synthesized surfactants such as surface tension reduction and temperature and pH stability enhancement (Ishigami et al., 1987. Chem. Lett., 763).

According to another embodiment of the present invention, the present invention provides a composition for washing and cleaning agents including the biosurfactant of Formula 1. Furthermore, biosurfactants have been widely used, without limitation, in a variety of industrial fields where chemically synthesized surfactants are used such as medicines, foods, cosmetics, detergents, secondary recovery of crude oil, pulp and paper industry, onshore and offshore oil decontamination, degradation of oil and fat in treatment tanks, and the like.

EXAMPLES

The following examples illustrate the invention and are not intended to limit the same.

Example 1

Isolation of L9 from *Aureobasidium pullulans* and Purification of the Same

*Aureobasidium pullulans* L-3-GPY was deposited at the Korean Culture Center of Microorganisms (KCCM) on Jul. 5, 2011 under accession number KCCM 11200P. 100 g of a sample prepared by concentrating a broth filtrate of *Aureobasidium pullulans* L-3-GPY isolated from *Lilium lanciforlium* Thunb was dissolved in water, and flash reversed-phase column chromatography was performed. Elution was attempted using 70% and 90% aqueous methanol, and a compound having activity according to an embodiment of the present invention was eluted in 90% aqueous methanol. The eluted active ingredient was concentrated under reduced pressure to remove methanol and treated with ethyl acetate (EA) to perform phase separation. As a result of measuring activity, activity was detected in the ethyl acetate phase. Then, ethyl acetate was concentrated under reduced pressure, and silica gel chromatography was performed using a solution of chloroform and methanol (chloroform:methanol=50:1→10:1 (v/v)) as a developing solvent. Fractions having activity were concentrated, and Sephadex LH-20 column chromatography was performed using 50% aqueous methanol. After the activity of the fractions was evaluated, fractions with activity were collected and concentrated under reduced pressure, and then chromatography was performed using a reversed phase ($C_{18-}$) Sepak cartridge. A solution with a gradient from 50% to 70% aqueous methanol was used as an elution solution. As a result, Compound L9 (3.7 mg) having activity was separated and purified. FIG. 1 shows an isolation and purification process of active ingredient L9 described above.

Example 2

Interpretation of Chemical Structure of Active Ingredient L9 Using Spectroscopy 1. Measurement and Interpretation of NMR Spectra In order to confirm the chemical structure of active Compound L9, Compound L9 was dissolved in $CD_3OD$, and $^1H$ NMR, $^{13}C$ NMR, DEPT, $^1H$—$^1H$ COSY, HMQC, HMBC, and NOESY spectra were measured and interpreted.

Figure 2:
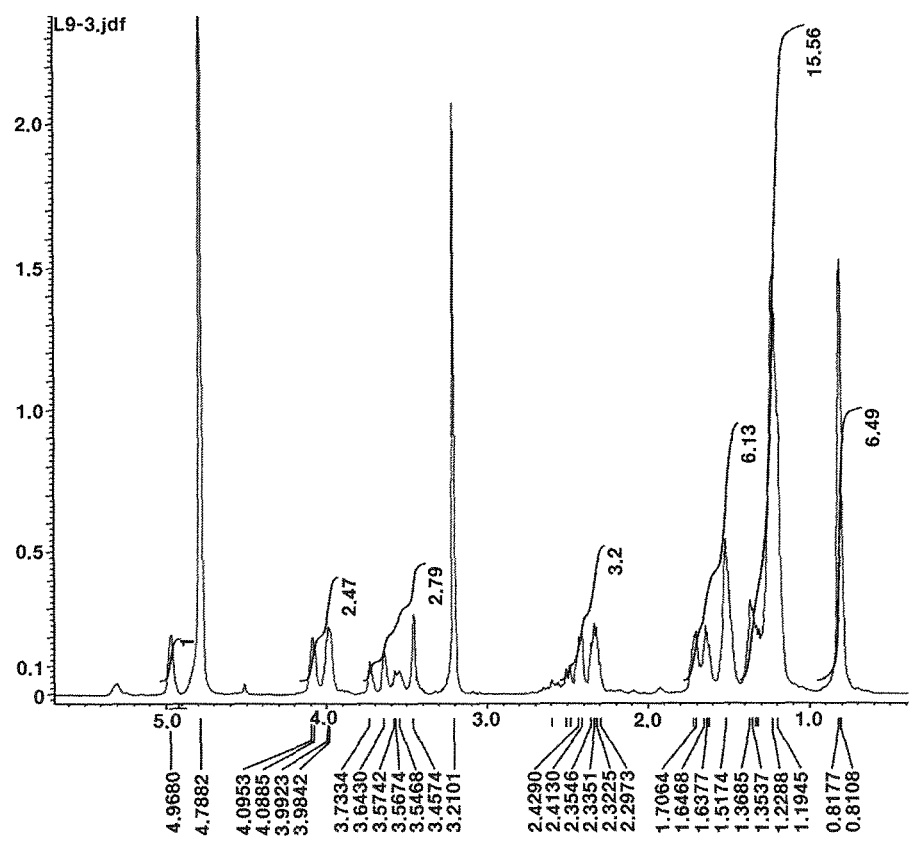
FIG. 2 shows numerical data of $^1$H NMR spectrum of Compound L9.

1) Measurement and Interpretation of $^1H$ NMR Spectrum:

As a result of measuring $^1H$ NMR spectrum (FIG. 2), 11 protons derived from oxygenated methines (tertiary carbons) and methylenes (secondary carbons) were observed at 3.5 to 5.0 ppm. In addition, 6 protons derived from three methylenes connected to a carbonyl group were observed at 2.4 to 2.6 ppm. Further, a plurality of methylene protons derived from an alkyl group were observed at 1.2 to 1.8 ppm, and 9 protons derived from three methyl groups were observed at around 0.8 ppm.

Figure 3:
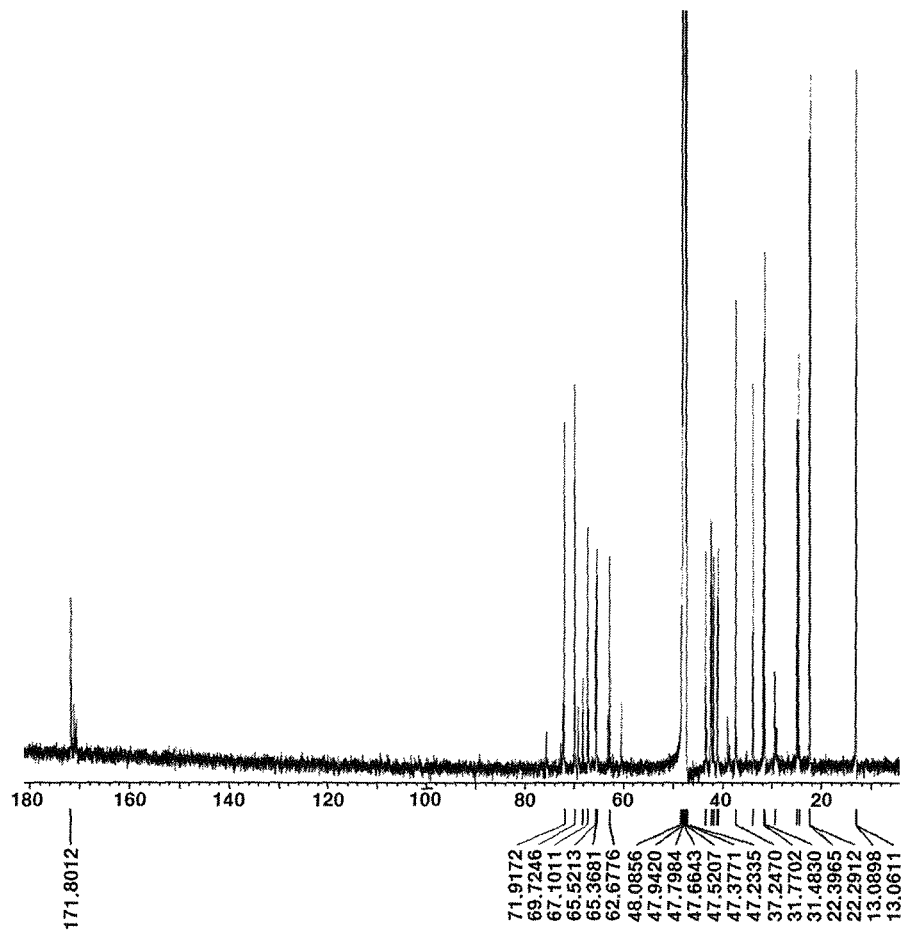
FIG. 3 shows numerical data of $^{13}$C NMR spectrum of Compound L9.

2) Measurement and Interpretation of $^{13}C$ NMR Spectrum:

As a result of measuring $^{13}C$ NMR spectrum (FIG. 3), three ester carbonyl carbon atoms were observed at 171.8 ppm, and 9 oxidized methine and oxidized methylene carbon atoms were observed at 62 to 72 ppm. In addition, a plurality of methine, methylene, and methyl carbon atoms derived from an alkyl group were observed at 13 to 44 ppm.

Figure 4:
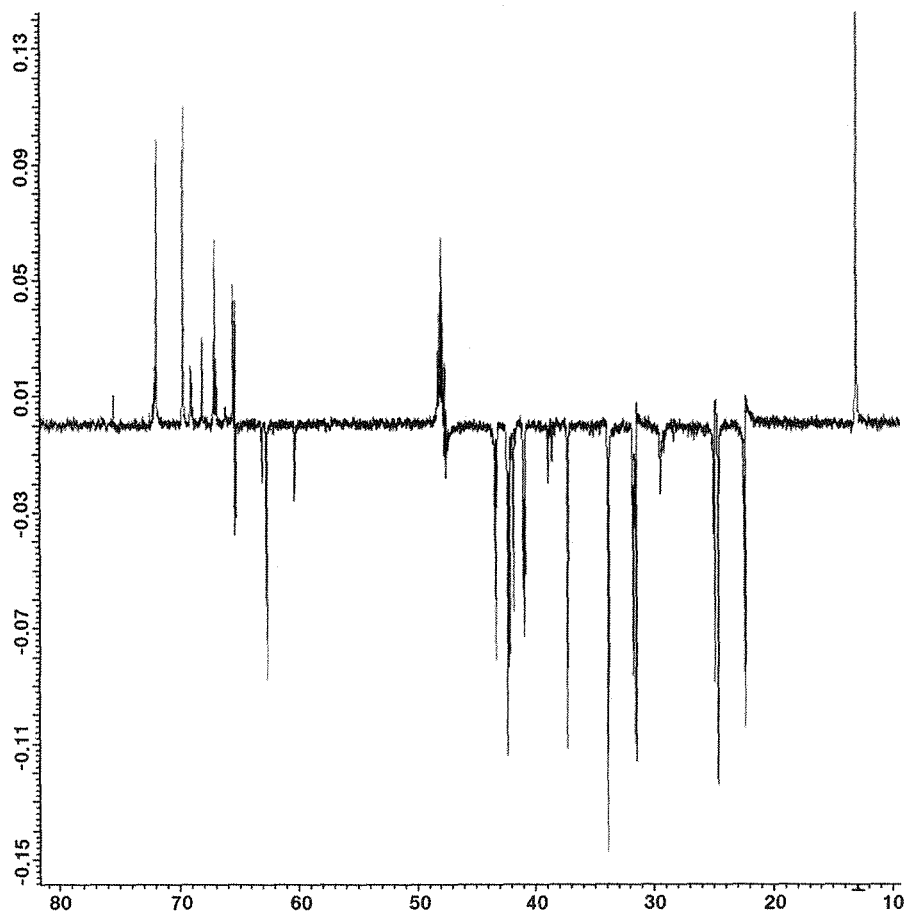
FIG. 4 shows numerical data of DEPT spectrum of Compound L9.

3) Measurement and Interpretation of DEPT Spectrum:

It was confirmed that the carbon atoms observed in the $^{13}C$ NMR spectrum were three methyl carbon atoms, 20 methylene carbon atoms, 7 methine carbon atoms, and 3 quaternary carbon atoms based on the measurement and interpretation of DEPT spectrum (FIG. 4).

Figure 5:
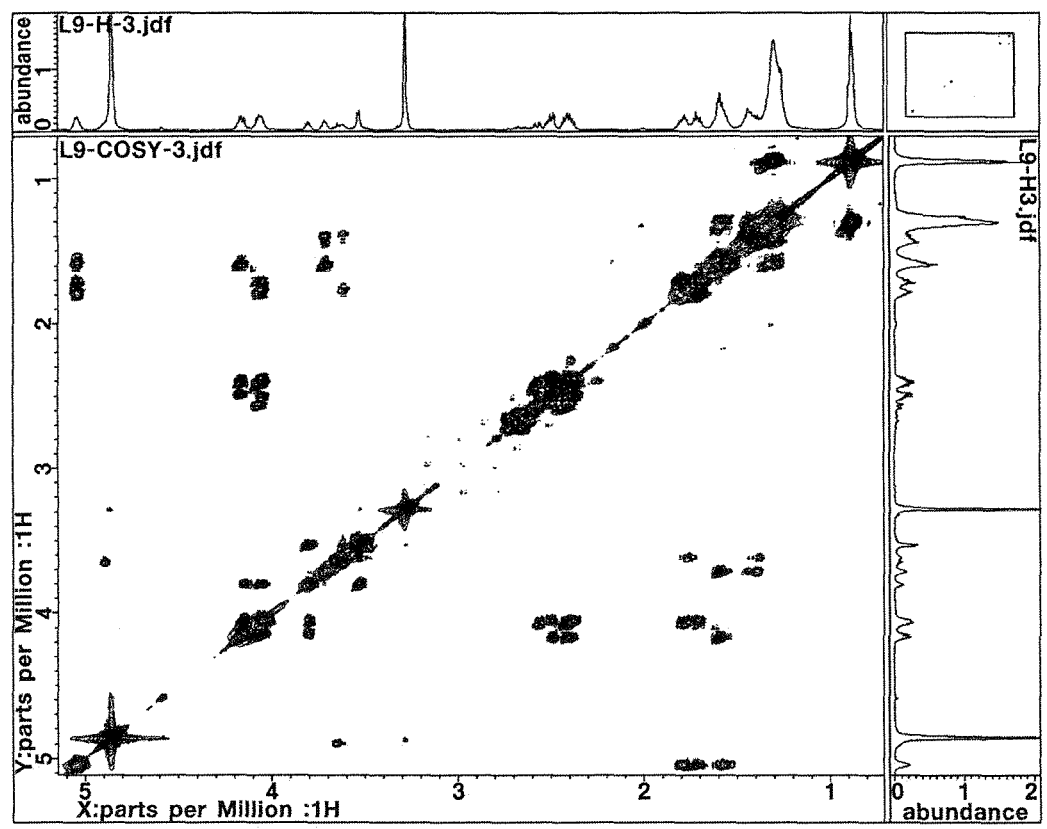
FIG. 5 shows numerical data of $^1$H—$^1$H COSY spectrum of Compound L9.
Figure 6:
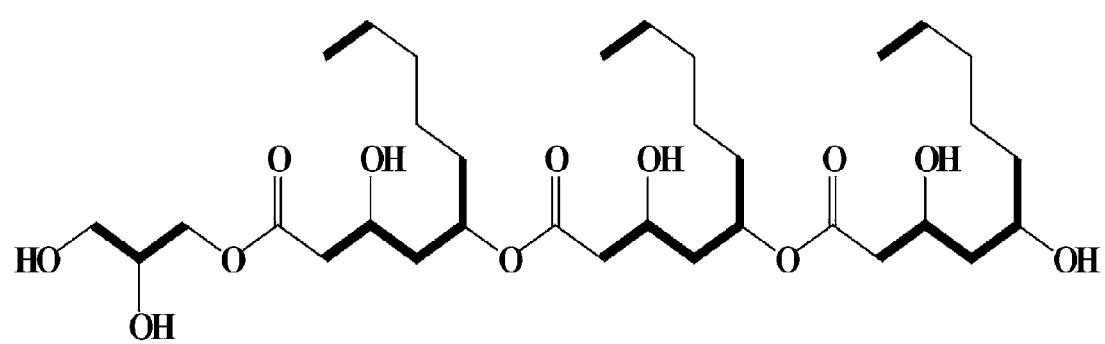
FIG. 6 shows a partial structure of Compound 9 confirmed by numerical data of $^1$H—$^1$H COSY spectrum of Compound L9 and shown using bold lines.

4) Measurement and interpretation of $^1H$—$^1H$ COSY spectrum:

In order to confirm a partial structure of Compound L9, $^1H$—$^1H$ COSY spectrum (FIG. 5), by which the correlation of $^3J_{H-H}$ could be detected, was measured and interpreted. As a result of the $^1H$—$^1H$ COSY spectrum interpretation, a partial structure derived from three acyl groups and a partial structure derived from glycerol were confirmed (FIG. 6). The partial structure derived from the acyl groups was not interpreted due to overlapping of spectral peaks, so a TOCSY spectrum was measured.

Figure 7:
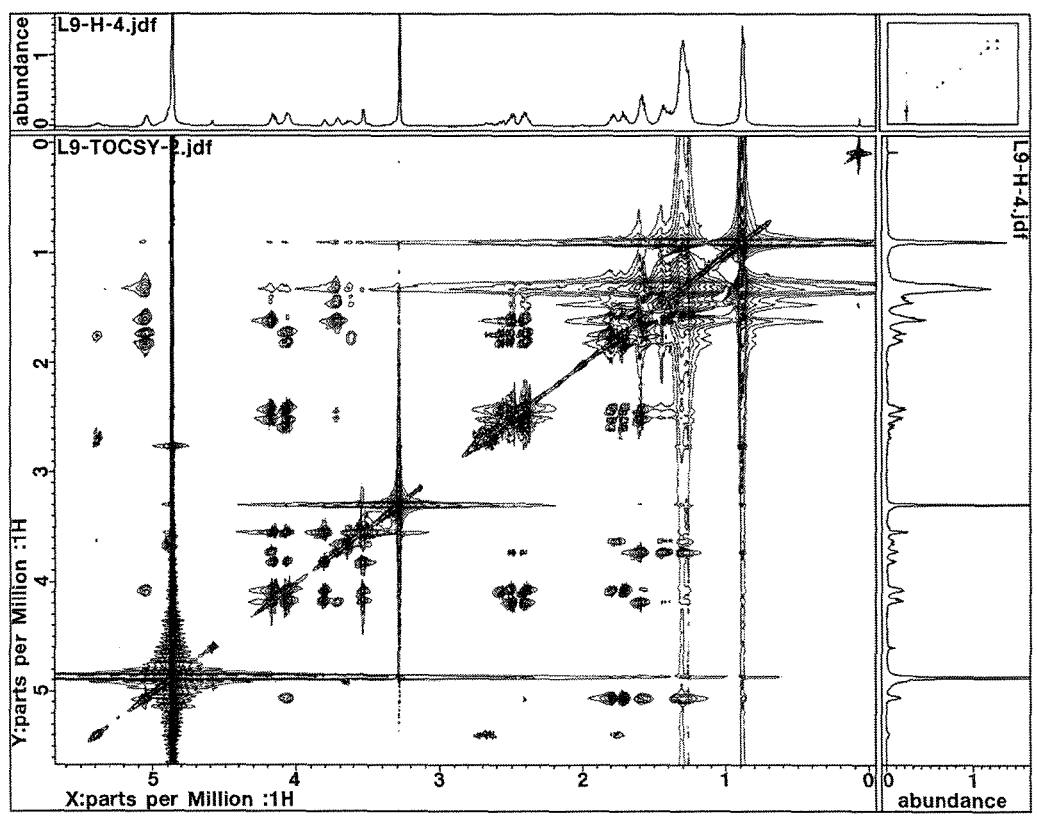
FIG. 7 shows numerical data of TOCSY spectrum of Compound L9.
Figure 8:
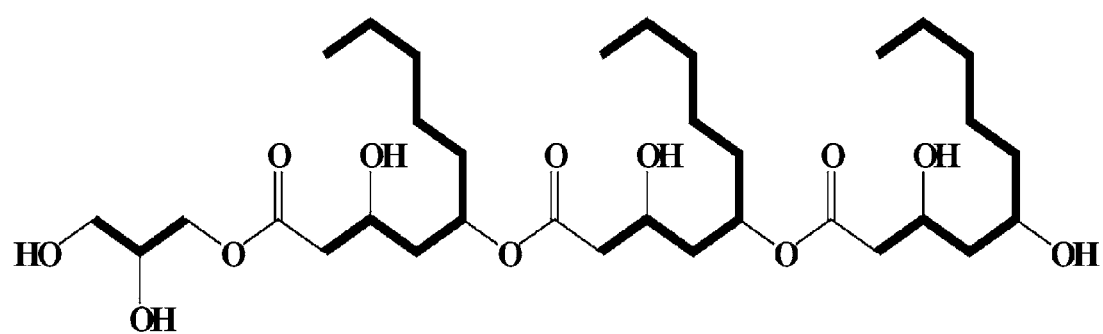
FIG. 8 shows a partial structure of Compound 9 confirmed by numerical data of TOCSY spectrum of Compound L9 and shown using bold lines.

5) Measurement and Interpretation of TOCSY Spectrum:

In order to investigate a partial structure of Compound L9 that was not interpretable due to spectral peak overlap, TOCSY spectrum (FIG. 7) was measured and interpreted. As a result of the TOCSY spectrum interpretation, the partial structure derived from the glycerol component was confirmed, and the partial structure derived from the three acyl chains was inferred as 3,5-dihydroxydecanoate (FIG. 8).

Figure 9:
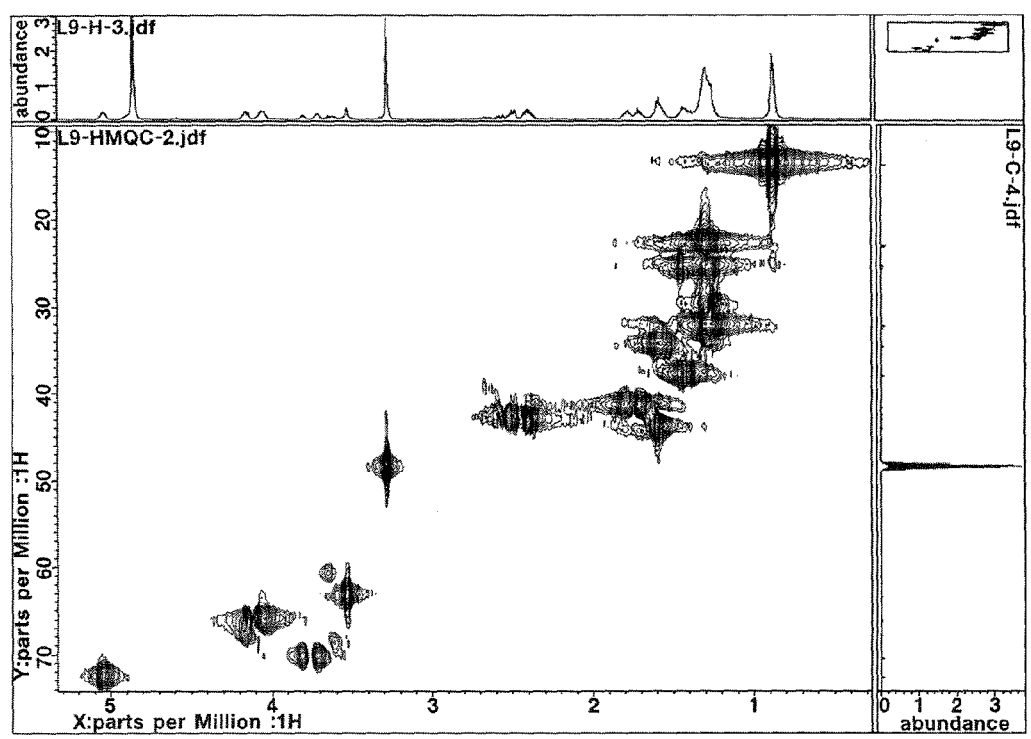
FIG. 9 shows numerical data of HMQC spectrum of Compound L9.
Figure 10:
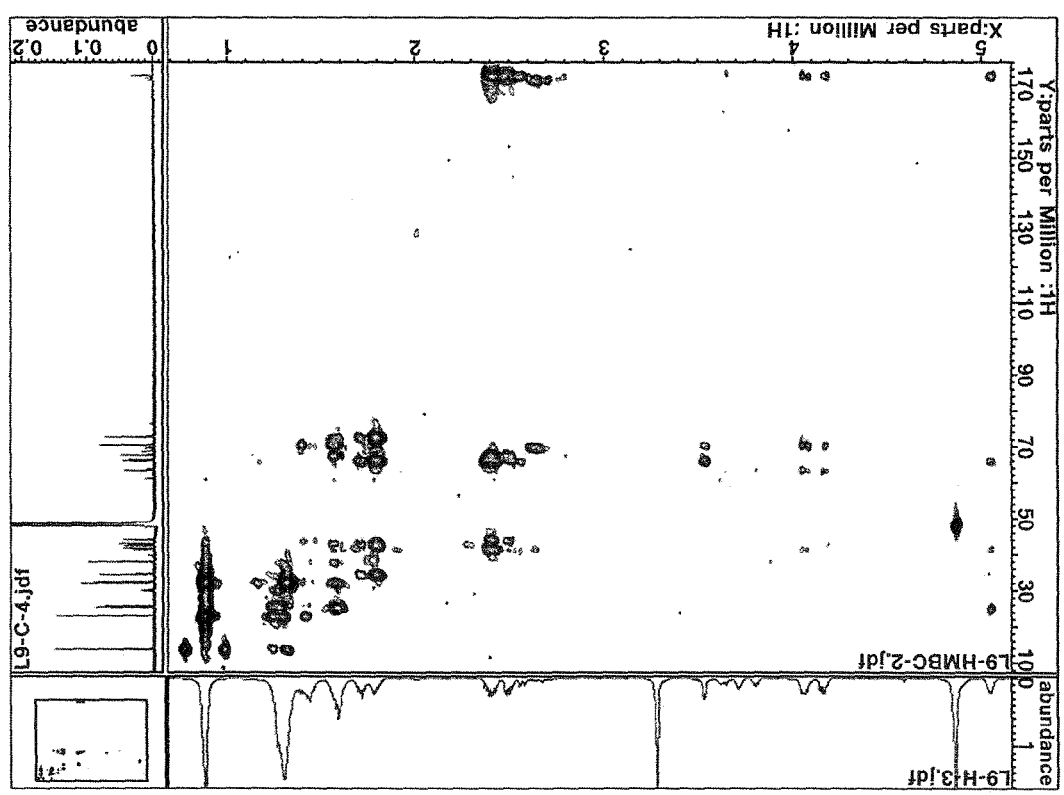
FIG. 10 shows numerical data of HMBC spectrum of Compound L9.
Figure 11:
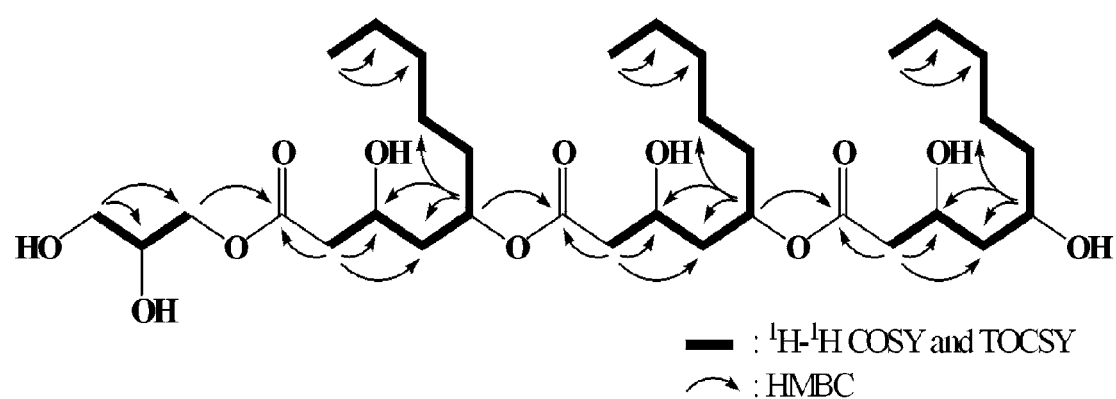
FIG. 11 shows a partial structure of Compound 9 confirmed by numerical data of HMBC spectrum of Compound L9 and shown using arrows, in which bold lines are confirmed by the $^1$H—$^1$H COSY spectrum and TOCSY spectrum.

6) Measurement and Interpretation of HMQC Spectrum and HMBC Spectrum:

As a result of measurement and interpretation of the HMQC spectrum (FIG. 9), all proton-bearing carbons ($^1J_{C-H}$) were assigned. In addition, as a result of measurement and interpretation of the HMBC spectrum (FIG. 10), a long-range correlation from an oxygenated methine proton at 5.0 ppm to methylene carbons at 24.6 and 24.9 ppm and oxygenated methine carbons at 65.5, 65.4, and 67.1 ppm and long-range correlations from methylene protons at 2.4 and 2.5 ppm to oxygenated methine carbons at 65.5, 65.4, and 67.1 ppm and an ester carbonyl carbon at 171.8 ppm were observed. Based on these results, this compound was suggested to be a trimer of 3,5-dihydroxydecanoic acid in which three partial structures of 3,5-dihydroxydecanoate form an ester bond with the oxygenated methine of the C-5 position of a neighboring unit. In addition, the long-range correlation between the methylene protons at 4.05 and 4.15 ppm constituting the glycerol moiety and a carbonyl carbon at 171.8 ppm was observed. This revealed that the glycerol moiety was connected to the carboxyl group of the trimer of 3,5-dihydroxydecanoic acid. Based on the above results, the chemical structure of Compound L9 was determined, as shown in FIG. 11, and this structure was determined to be a novel compound confirmed from a database search.

2) Measurement and Interpretation of Mass Spectrum (MS)

Figure 12:
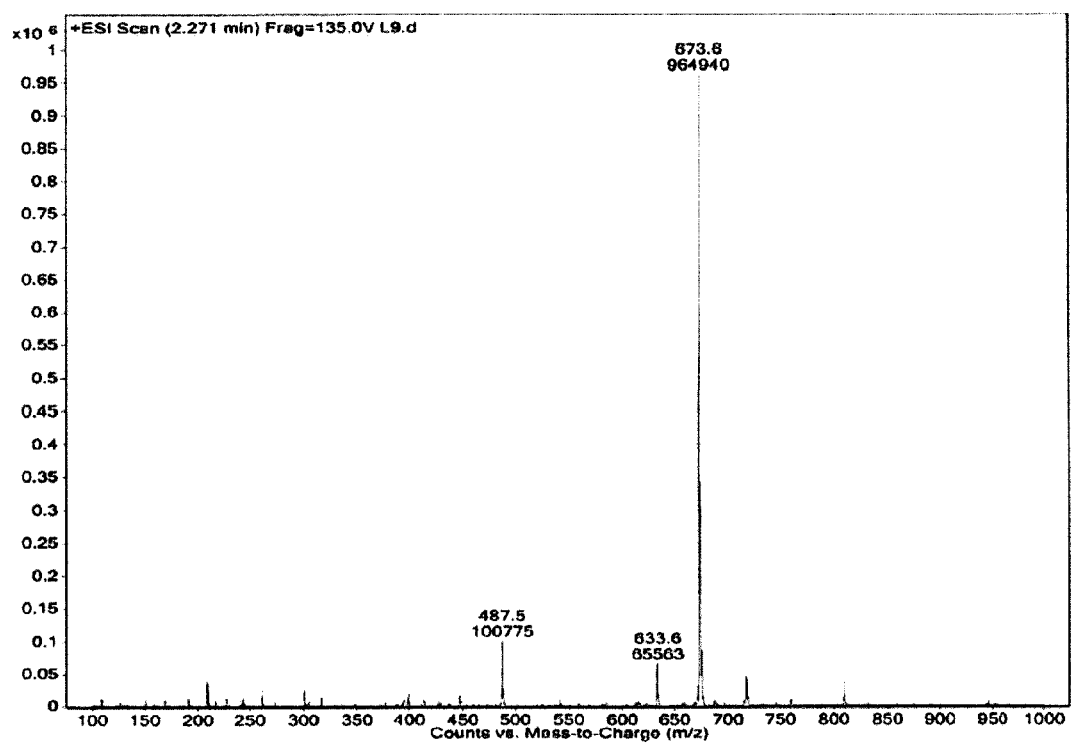
FIG. 12 shows numerical data of ESI-mass analysis of Compound L9.
Figure 13:
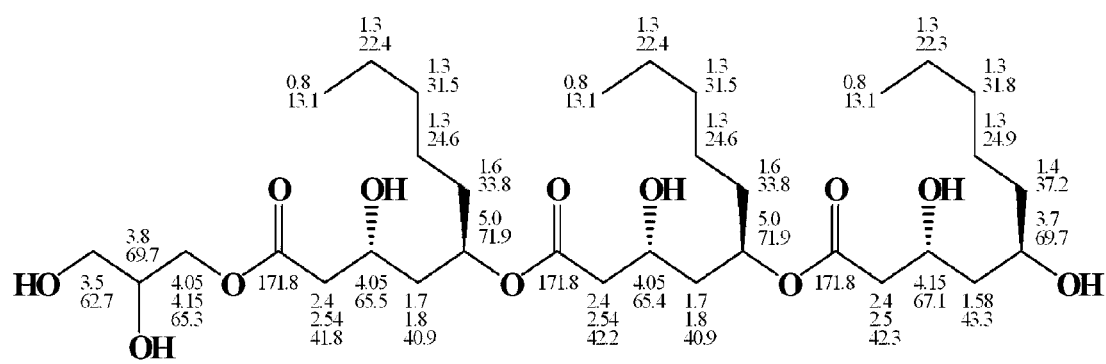
FIG. 13 shows a three-dimensional structure of Compound L9 and numerical data of $^1$H NMR spectrum and $^{13}$C NMR spectrum.

The chemical structure of the active compound was determined to be novel based on the NMR spectra. In order to confirm the NMR results, mass spectroscopy analysis was performed. As a result of measuring ESI-mass spectrum (FIG. 12) in the positive mode, [M+Na]$^+$ was observed at m/z 673.6, and it was confirmed that the molecular weight of the compound was 650. This molecular weight corresponded identically with the chemical structure determined by using the NMR spectroscopy.

Example 3

Observation of Performance as Surfactant

1) Measurement of Surface Tension

Figure 14:
FIG. 14 is a picture of the surface tension of an aqueous solution of Compound L9 dropped on a hydrophobic film.

Compound L9 isolated in Example 1 was dropped on a hydrophobic film, and surface tension variation was observed using a surface tension meter (Densitometer, Sigma 700 Densitometer (KSV Instruments Ltd., Finland)). Water was a control, and a culture medium and the size of compound L9 were compared. The results are shown in FIG. 14.

As intermolecular interaction increases, surface tension increases. Since hydrocarbons, organic polymers, and the like have week intermolecular interactions, the surface tension thereof is low.

The numerical value of the surface tension was shown as (dyne/cm (or mN/m)). When a surfactant that has a hydrophobic moiety and a hydrophilic moiety is added to water, surface tension decreases. Table 1 below shows surface tension of water, mercury, and glycerin. As the intermolecular interaction increases, the surface tension increases.

Compound L9 according to the present invention showed a low surface tension of 31.5 mN/m at 1.5 mg/litter. Water as a control showed a surface tension of 72.8 dyne/cm. Thus, Compound L9, that is a biosurfactant, was confirmed as a good surfactant.

TABLE 1

| | Surface tension (dyne/cm) |
|---|---|
| L9 | 31.5 |
| Water | 72.8 |
| Mercury | 486 |
| Glycerin | 63 |

2) Comparison Between Compound L9 and Compounds Having Known Surfactant Activity Surface tensions of Compound L9 and known materials produced by bacteria (Table 2) and yeasts (Table 3) were measured, and the results are shown in Tables 2 and 3 below.

TABLE 2

| Name of material | Name of bacteria strain | Amount of material (mg/L) | Surface tension (dyne/cm) |
|---|---|---|---|
| L9 | *Aureobasidium pullulans* sp. L-3-GPY | 1.5 | 31.5 |
| Flavolipid | *Flavobacteriium* sp.strain MTN11 | 300 | 26.0 |
| Rhamnolipid | *Pseudomonas aeruginosa* UG3 | 30 | 31.4 |
| Trehalose lipid | *Rhodococcus erythropolis* DSM43215 | 0.7 | 43.0 |
| Trehalos lipid | *Micrococcus luteus* BN56 | 25 | 24.1 |
| Iturin | *Bacillus subtilis* S499 | 20 | 43.0 |

TABLE 3

| Name of material | Name of yeast strain | Amount of material (mg/L) | Surface tension (dyne/cm) |
|---|---|---|---|
| Sophorolipid | *Candida bomibocola* ATCC 22214 | 40 | 35.0 |

Since the surface tension of Compound L9 according to the present invention was 31.5 dyne/cm when the amount of Compound L9 was 1.5 mg/L, it was confirmed that Compound L9 showed lower surface tension than other materials known to have surfactant activity at a very lower amount. Accordingly, it was confirmed that Compound L9 has better surfactant activity than known surfactants.

[Deposition]
Name of depositary institution: Korean Culture Center of Microorganisms (KCCM) (overseas)
Accession number: KCCM11200P
Date of deposit: Jul. 5, 2011

Features and advantages of the present invention are summarized as follows.

(i) A compound having biosurfactant activity and produced from *Aureobasidium pullulans* L-3-GPY strains according to an embodiment of the present invention is a novel compound.

(ii) The biosurfactant produced by *Aureobasidium pullulans* has a high degree of activity of 31 dyne/cm so as to be used for washing and cleaning agents. In addition, the biosurfactant can also be used in most of various industrial fields where chemically synthesized surfactants are used such as medicines, foods, cosmetics, onshore and offshore oil decontamination, degradation of oil and fat in a treatment tank, and the like.

The invention has been described in detail with reference to exemplary embodiments thereof. However, it will be appreciated by those skilled in the art that changes may be made in these embodiments without departing from the principles and spirit of the invention, the scope of which is defined in the appended claims and their equivalents.

What is claimed is:

1. A compound produced by *Aureobasidium pullulans* L-3-GPY KCCM11200P strains and represented by Formula 1 below:

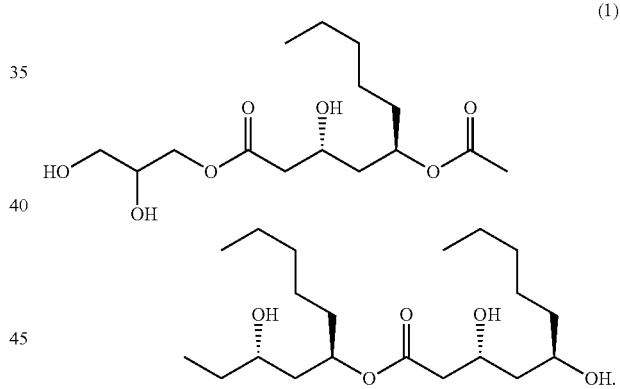

(1)

2. The compound of claim 1, wherein the compound represented by Formula 1 is a biosurfactant.

3. A composition for washing and cleaning agents comprising the biosurfactant of Formula 1 of claim 2.

4. A composition for cosmetics comprising the biosurfactant of Formula 1 of claim 2.

* * * * *

UNITED STATES PATENT AND TRADEMARK OFFICE
CERTIFICATE OF CORRECTION

| | | |
|---|---|---|
| PATENT NO. | : 8,642,793 B1 | Page 1 of 1 |
| APPLICATION NO. | : 13/692681 | |
| DATED | : February 4, 2014 | |
| INVENTOR(S) | : Jong Shik Kim et al. | |

It is certified that error appears in the above-identified patent and that said Letters Patent is hereby corrected as shown below:

In the Specification

Col. 6, lines 64 and 65, Densitometer should read

-- Tensiometer --

Signed and Sealed this
Twenty-second Day of April, 2014

Michelle K. Lee
*Deputy Director of the United States Patent and Trademark Office*